United States Patent
Larson et al.

(10) Patent No.: US 6,776,757 B2
(45) Date of Patent: *Aug. 17, 2004

(54) IN VIVO BIOCOMPATIBLE ACOUSTIC COUPLING MEDIA

(75) Inventors: Margaret J. Larson, Lummi Island, WA (US); John W. Rutter, Bellingham, WA (US); Larry L. Smith, Seattle, WA (US)

(73) Assignee: Sonotech, Inc., Bellingham, WA (US)

( * ) Notice: Subject to any disclaimer, the term of this patent is extended or adjusted under 35 U.S.C. 154(b) by 77 days.

This patent is subject to a terminal disclaimer.

(21) Appl. No.: 09/904,683

(22) Filed: Jul. 13, 2001

(65) Prior Publication Data

US 2001/0039380 A1 Nov. 8, 2001

Related U.S. Application Data

(63) Continuation-in-part of application No. 09/346,463, filed on Jul. 1, 1999, now Pat. No. 6,302,848.

(51) Int. Cl.$^7$ ............................................. A61B 8/00
(52) U.S. Cl. ............................................ 600/437
(58) Field of Search .................. 73/620, 642, 621, 73/646; 600/437, 461; 607/152; 424/1.21, 1.25, 1.33, 9.3, 9.321, 9.322, 9.5, 9.51, 445–447; 521/139–141; 525/7, 10

(56) References Cited

U.S. PATENT DOCUMENTS

| | | |
|---|---|---|
| 4,002,221 A | 1/1977 | Buchalter |
| 4,459,854 A | 7/1984 | Richardson et al. |
| 4,593,699 A | 6/1986 | Poncy et al. |
| 4,994,227 A | 2/1991 | Dietz et al. |
| 5,078,149 A | 1/1992 | Katsumata et al. |
| 5,093,319 A | 3/1992 | Higham et al. |
| 5,259,383 A | 11/1993 | Holstein et al. |
| 5,266,326 A | 11/1993 | Barry et al. |
| 5,342,617 A | 8/1994 | Gold |
| 5,405,366 A | 4/1995 | Fox et al. |
| 5,676,159 A | 10/1997 | Navis |
| 5,773,024 A | 6/1998 | Unger et al. |
| 5,873,367 A | 2/1999 | Buchalter |
| 6,146,657 A | 11/2000 | Unger et al. |
| 6,302,848 B1 | 10/2001 | Larson et al. |

FOREIGN PATENT DOCUMENTS

| | | |
|---|---|---|
| DE | 4400039 | 7/1995 |
| EP | 0420758 | 4/1991 |
| JP | 55-63636 | 5/1980 |

OTHER PUBLICATIONS

WPI Abstract No. 1995–241601 (DE 44 00 039 to Loehnert).
Doelker, E., "Water–Swollen Cellulose Derivatives in Pharmacy", *Hydrogels in Medicine and Pharmacy: vol. 2 —Polymers*, edited by Peppas, N. A., CRC Press Inc., Boca Raton, Florida, 1987, p. 124.
WPI—Japanese Patent Abstract JP55063636.
WPI—Japanese Patent Abstract JP3114453.

*Primary Examiner*—Francis J. Jaworski
(74) *Attorney, Agent, or Firm*—Robert L. McDowell

(57) ABSTRACT

A medical ultrasound coupling media and lubricant, in gel or liquid form, comprised of polyethylene oxide (PEO), at least one of polyalkylene glycols and polyhydric alcohols, and the balance water. The inventive coupling media provides long-term biocompatibility (bio-inert, bio-erodable or biodegraded and excreted) in vivo with human tissue and body fluids. The ultrasound coupling and lubricating media is formulated and manufactured in such manner and form that produces higher viscosity gels with decreased amounts of polymer and renders the acoustic media sterile, non-cross-linked, pseudoplastic, and containing acceptably low levels of pyrogens.

20 Claims, 2 Drawing Sheets

IN VIVO BIOCOMPATIBLE ACOUSTIC COUPLING MEDIA

This application is a continuation-in-part of application Ser. No. 09/346,463 filed Jul. 1, 1999 now U.S. Pat. No. 6,302,848.

FIELD OF THE INVENTION

The present invention is directed toward the medical use of acoustic coupling gels and fluids used in ultrasound imaging and doppler based flow measurement during procedures that invade the body, such as ultrasound guided biopsy, ophthalmic imaging, during surgery and intracavity examinations.

BACKGROUND OF THE INVENTION

It is well known to introduce chemical substances into a body in which the chemical substances contact body tissue. One obvious example is introducing medication in pill form into a human or animal. Aside from the particular active ingredient, the pill may comprise different types of waxes, fats, and filler or wetting agents, all of which must not react with body tissue. One such example can be found in U.S. Pat. No. 4,994,227 to Dietz et al.

In medical procedures such as surgery, it is known to introduce chemical substances into a body cavity and in contact with vital tissues. One such example is disclosed in U.S. Pat. No. 5,093,319 to Higham et al. where adhesion or inflammation of tissues after surgery is prevented by placing a material made up of biodegradable derivatives of chitin between the tissues. Another example of the prevention of post-operative adhesions is found in U.S. Pat. No. 5,266,326 to Barry et al. where polysaccharides, such as alginates, and a complexing agent, such as calcium chloride, are combined in situ between affected tissues to form a biodegradable gel. U.S. Pat. No. 5,405,366 to Fox et al. teaches the production of cohesive, non stringy cross-linked gels for the delivery of therapeutic drugs to wound sites by subjecting solutions, such as that of polyethylene oxide in combination with other compounds, to high energy radiation.

With some current surgical procedures, as the uses and technology of medical ultrasound imaging have evolved, imaging procedures that were once performed externally over skin surfaces are now being performed in contact with organs, tissue and body cavity mucosa. For example, when imaging the liver during surgery, the transducer is often placed directly on its surface.

Ultrasound, as used for medical applications, utilizes high frequencies, typically between 1 and 20 MHz for imaging and flow measurements, which are poorly transmitted by air and requires a coupling or conduction medium similar in acoustic properties to tissue, commonly a thick fluid or gel, to transfer the acoustic energy between the body and the electronics. The ultrasound coupling gel or fluid displaces air and fills contours between the piezoelectric transducer or "eye" of the instrument, which converts energy between electrical and acoustic, and the body into which the sound is being directed. This gel or fluid material, by nature of its physical and acoustic properties, serves as an ultrasound acoustic coupler between the body and the electronic transducer, thereby acoustically joining the two, so that the ultrasound based information developed, can freely pass back and forth between the body and the transducer. The gel or fluid material may also serve as a lubricant to aid in the introduction of a medical device used for imaging, such as endoscopes, into the body.

Because of the coupling effect, this media is commonly referred to as an ultrasound couplant, ultrasound gel, ultrasound transmission media or acoustic transmission media. Many fluids and water-based gels have been used as ultrasound couplants over the years. Early use of mineral oil was replaced by gels of water and acrylic based polymers such as CARBOPOL® (a registered trademark of BF Goodrich Specialty Chemicals) typical of those described in U.S. Pat. No. 4,002,221 to Buchalter, and also gels made from acrylic polymers and attached as coupling members to transducers such as are described in U.S. Pat. No. 4,459,854 to Richardson et al. as a method for improvement of perivascular blood flow measurement.

Use of currently available ultrasound coupling fluids and gels of prior art in surgical, and ultrasound guided needle puncture procedures have fundamental disadvantages that place the patient at risk. Some of these disadvantages are described below:

1. Oils or thickened water-based gels typically used in medical ultrasound are similarly described as in previously discussed U.S. Pat. No. 4,002,221, and are comprised of chemical compounds such as acrylic polymers, carboxy alkyl cellulose, hydroxyethylcellulose, carboxy polymethylene, polyalkylene glycol humectants, organic acids, alkali metal salts, parabens and other germicidal and fungicidal agents, and surfactants that are unsuitable for use in applications where they may be carried into the body tissue or fluids.

2. The above-mentioned couplants are also commercially available in sterilized form, thus implying and encouraging their inappropriate use in vivo where their chemical constituents are either known to be harmful to the human body or have not been evaluated for their in vivo use.

3. Currently available ultrasound couplants supplied in sterile form contain acrylic polymers such as CARBOPOL as a common and primary ingredient. CARBOPOL, for example, has not been tested for in vivo biocompatibility. Some currently available sterile couplants also contain cellulose ethers to increase salt stability. According to E. Doecker in "Water Swollen Cellulose Derivatives in Pharmacy" from *Hydrogels in Medicine and Pharmacy: Vol. 2-Polymers*, edited by Peppas N. A., CRC Press Inc., Boca Raton, Fla., 1987, pg. 124, "In common use, such celluloses are used orally and externally, however parenteral administration of celluloses is not recommended since derivatives are not easily metabolized". Since various chemicals of these formulations are not in vivo biocompatible, they can remain in the body as substances that can cause inflammation, disruption in flow of lymph, irritation, anaphylactic shock and other immune system reactions. This concern becomes apparent during ultrasound guided needle biopsy or aspiration, or inside the body when ultrasound transducers encapsulated in fragile sheaths containing sterile ultrasound couplant are inserted for imaging during surgery in direct contact with organs, tissue and blood.

Of additional concern are the unknown chemical constituents formed during sterilization processing. Methods of couplant sterilization include steam autoclave, E-beam, broad spectrum light and gamma radiation protocols. Couplant products that incorporate CARBOPOL in the formulation can break down as a result of heat during autoclaving. When exposed to ionizing radiation, such as in the case of gamma and E-beam, and high intensity light sterilization, free radicals can be formed, and chain scission and cross linking of the polymer can occur, as evidenced by presence of bubbles and changes in color, viscosity and mechanical properties of the polymer products.

It is important to note that sterility of a substance does not guarantee that it is biocompatible, or of greater importance, in vivo biocompatible. When a substance is sterile, it does not contain live microorganisms; however, such sterile materials may not be in vivo-biocompatible should they contain compounds that are incompatible with tissue or body fluids. For example, natural and synthetic materials that are recognized by the FDA as GRAS (Generally Regarded As Safe) may not be in vivo biocompatible. An in vivo biocompatible substance is both sterile, containing no living micro-organisms, and contains no chemicals or substances that are toxic or cause inflammation or immune system reactions, such as from pyrogens, within the living human body. A substance such as the device of this invention is in vivo biocompatible as an ultrasound couplant in contact with human tissue and body fluids.

4. In instances where sterile latex rubber or synthetic "sheaths" containing thickened chemical ultrasound coupling gels are used to encapsulate the ultrasound transducer during surgery, such as described in U.S. Pat. No. 5,259,383 to Holstein et al.; U.S. Pat. No. 4,593,699 to Poncy et al. and U.S. Pat. No. 5,676,159 to Navis; tearing, cutting, or rupture of the sheath can result in the bio-incompatible ultrasound couplant spilling into the body cavity. During procedures such as transcutaneous biopsy or aspiration of fluid under ultrasound imaging guidance, such bio-incompatible ultrasound couplants of the prior art are placed directly on the skin covering the area of the biopsy. A biopsy needle can carry such chemicals into the body, such as into the breast or into amniotic fluid.

It is an object of the present invention to provide an ultrasound couplant and device lubricant suitable for the medical use of ultrasound acoustic energy for imaging and doppler based flow measurement, while contacting body tissue, fluids and organs, during transcutaneous biopsy and fluid aspiration, and to lubricate the passage of the imaging device into body cavities.

It is a further object of the present invention to provide gels and fluids that are in vivo biocompatible, and suitable for use in diagnostic ultrasound procedures inside the body of a human during surgery, guided biopsy, within body cavities and ophthalmic imaging.

SUMMARY OF THE INVENTION

The device of this invention is an in vivo biocompatible lubricant and ultrasound coupling fluid or gel in a non-cross-linked form, produced from compounds based on polyethylene oxide (PEO), and in particular PEO in pure form, that are biodegradable or bio-inert, having known and acceptable biological effects on tissue and the immune system of the human body. The inventive couplant fluid or gel may additionally contain polyalkylene glycols and polyhydric alcohols. The inventive couplant fluid or gel can remain in the body or be excreted from the body after being eroded, metabolized or absorbed via natural pathways and processes. In sterile form, the inventive in vivo biocompatible couplant and device lubricant is intended for use in contact with organs, tissue and body fluids during surgery, intracavity, and ultrasound guided needle puncture procedures. The inventive couplant renders acceptable low levels of artifact, distortion and attenuation of ultrasound energy.

In instances where an ultrasound probe is covered by a protective sheath, as previously mentioned, the ultrasound couplants of the present invention not only provide acceptable acoustic coupling properties on the outside of the protective sheath but also within the sheath (i.e. between the ultrasound probe and the sheath). Thus, in the event of rupture of the sheath, introduction of the inventive ultrasound couplant into the body in contact with tissue, organs and fluids, will not adversely affect the patient due to the in vivo biocompatibility of the couplants of the present invention.

In the same manner, puncture procedures under ultrasound imaging guidance, such as needle biopsies, can benefit from the present invention in that the ultrasound couplant carried by the needle into the body will be an in vivo biocompatible couplant, thus posing no harm to tissue and organs.

For use in intraoperative procedures, the inventive couplant is placed inside the protective probe cover to couple the ultrasound acoustic energy between the active area of the probe and the cover or sleeve. Since during a surgical or intracavity ultrasound examination, the external surface of the probe cover is in contact with body fluids that naturally conduct acoustic energy, and therefore, additional couplant on the external surface is seldom required. For intracavity, i.e. vaginal, rectal and transesophageal ultrasound examinations, a lubricant is often required on the exterior of the transducer probe cover or the endoscope shaft prior to introduction into the body cavity. When such couplants are used for transcutaneous scanning, ophthalmic imaging or ultrasound guided needle punctures, such as amniocentesis and transcutaneous biopsy procedures, additional couplant is required to couple sound between the external surface of the protective cover or sleeve and the patient. Such couplant is usually placed on the skin of the patient in the area of interest.

As stated above, a compound that achieves the objectives of this invention, that is; possesses in vivo biocompatibility, is polyethylene oxide (PEO). Polyethylene oxide, in amounts varying between 0.05 and 65% by weight, and the balance water, preferably pyrogen free water, and optionally further including at least one of polyalkylene glycols and polyhydric alcohols in the amounts varying between about 1.0 and about 90% by weight. When prepared in final form, such mixtures exhibit acoustic properties similar to that of human tissue, renders acceptable low levels of artifact, distortion and attenuation of the ultrasound energy, and acceptable viscosity, film forming and adherence characteristics.

DETAILED DESCRIPTION OF THE PREFERRED EMBODIMENTS

Figure 1:
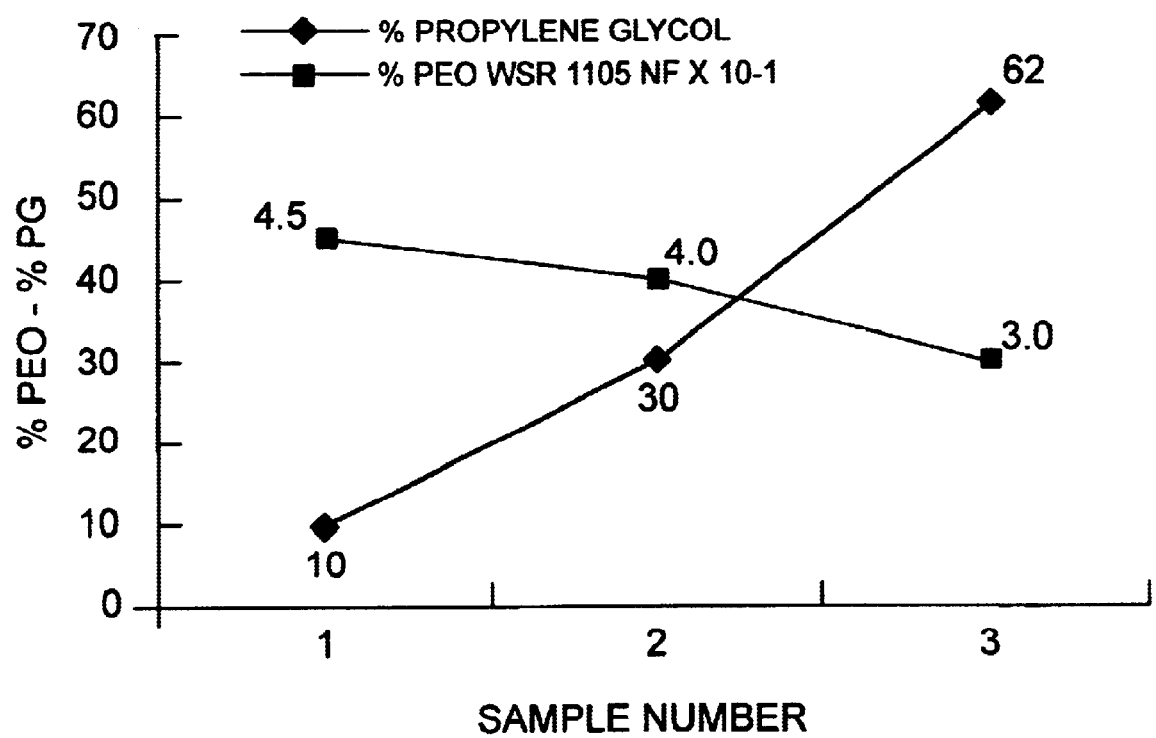
FIG. 1 illustrates the relationship between the weight percent (wt. %) of propylene glycol and the amount of PEO that is required to produce equivalent polymer viscosities as the amount of propylene glycol increases.

The present invention is directed toward the medical use of acoustic coupling fluids and gels used in vivo ultrasound imaging, doppler based flow measurement and in ultrasound guided transcutaneous biopsy.

The present invention is a medical device lubricant and ultrasound coupling media in a non-cross-linked gel or liquid form, comprised of polyethylene oxide (PEO), humectants and water, with known and acceptable long term interaction in vivo and is manufactured in such manner and form that renders the acoustic media sterile and biocompatible with human tissue, organs and body fluids.

A group of compounds based on polyethylene oxide (PEO) and in particular PEO in pure form, as a solution in water and containing acceptably low levels of pyrogens, is the preferred composition that demonstrates the desired in vivo biocompatibility and known in vivo biodegradability. Polyethylene oxide based biocompatible compounds and gels when properly formulated with water, and alternatively, PEO in combination with water and humectants such as polyalkylene glycols and/or polyhydric alcohols, have acoustic properties similar to that of human tissue, and render acceptable low levels of artifact, distortion and attenuation of the ultrasound energy.

As one embodiment of this invention, PEO is prepared in solution with pure, pyrogen free water. PEO in concentration amounts of about 0.05% to about 65% by weight and of various molecular weights, in the range of about 100,000 to about 8,000,000, can be used to form pseudoplastic solutions tailored to rheological properties desired for the application. As a modification to this base formulation, at least one of (1) polyalkylene glycols and/or fats and esters thereof, preferably containing 2 or greater carbon atoms and more preferably 2 to 6 carbon atoms, and (2) polyhydric alcohols, in a wt. % range of about 1% to about 90%, preferably about 10% to about 70%, is incorporated in the formulation. Preferably the polyalkylene glycols comprise propylene glycol and/or glycerol, most preferably propylene glycol. Preferably, the polyhydric alcohols comprise sorbitol. Propylene glycol is preferred since it is biocompatible, and biodegradable, and in a preferred embodiment functions as a humectant to increase drying time, and as a preservative and stabilizer that enhances the shelf life of PEO solutions.

To produce a biocompatible ultrasound couplant from PEO that has acceptable low levels of artifact, distortion, and attenuation, the couplant must be produced essentially free of air bubbles, undissolved polymer or insoluble particulate material. Application of Good Manufacturing Procedures (GMP) and use of NF PEO, USP propylene glycol or glycerol and pyrogen free water are recommended to ensure finished product quality.

Proper blending techniques are necessary to facilitate solution of the polymer in water. Properties that affect ease of solution include molecular weight, polymer concentration, rate of viscosity increase, rate of addition, particle size and the type and speed of agitation employed. It is necessary to obtain good dispersion of the polymer before the viscosity increases to a point where the resin cannot be further dispersed without introduction of high shear. On a laboratory scale, a multi-propeller stirrer is used to create a large vortex at about 600 rpm, followed by addition of POLYOX (PEO resin manufactured by Union Carbide) at a rate that fully disperses the resin. Once dispersion is achieved, the stirring rate is reduced to 50 to 60 RPM and stirred for 30 to 60 minutes until the PEO is dissolved and the solution is homogenous. When larger quantities of resin need to be dissolved, particularly if dry resin is added directly to water, equipment such as an eductor/disperser and multi-propeller or standard turbine type stirrers are recommended for ease of solution.

When polyalkylene glycols are incorporated into the formulation, alternative production methods can be used that facilitate efficient addition and dispersion of the polymer. A PEO slurry is first prepared by blending the dry polymer with the polyalkylene glycol, followed by addition of this polymer slurry directly into water or in the alternative, addition of water to the polymer slurry while stirring, thus reducing dust and the tendency to clump as is common to direct addition of dry polymer to water.

Techniques successful in limiting and removing entrapped air from PEO solutions involve a "de-airing" of the water used in the solution. This can be accomplished by heating and holding at 60° C. for 2 hours followed by addition of the PEO. In practice, if cooling is desired, accelerated cooling of the water limits the amount of gases that re-absorb. Removal of air entrapped during addition of PEO polymer and high-speed stirring is accomplished by applying a minimum of 25 inches of vacuum after addition of the polymer. Subsequent backfill of the vessel head-space with nitrogen or other inert gas reduces the amount of viscosity loss since it reduces the amount of oxygen available to react with and break down the polymer chains.

For use as in vivo biocompatible ultrasound couplants, the polymer solution must be sterilized. The common and acceptable sterilization methods of e-beam and gamma irradiation tend to be unsuitable for polyethylene oxide formulations. Radiation dosages prescribed for sterilization protocols, generally 15 KGY and above, are sufficient to cross-link or degrade polyethylene oxide solutions. Such response to high energy exposure decreases lubricity and pseudoplastic behavior by either creating insoluble solids and cohesive masses that are unsuitable for ultrasound imaging procedures or it breaks the polymer bonds, thus reducing the viscosity to approximately that of the base fluid. As an example, U.S. Pat. No. 5,405,366 to Fox et al. teaches methods to produce cross-linked polyethylene in combination with other compounds such as PVA and gylcols, by subjecting combinations of these compounds to high-energy radiation sufficient to form cross-linked compounds that are non-stringy and cohesive. Such cross-linked compounds; however lack the physical properties preferred for use as ultrasound couplants and lubricants.

One embodiment of the present invention describes pseudoplastic, non cross-linked solutions of PEO, water and alternatively, glycols, which are preferably sterilized by heat to avoid cross-linking. Given the constraints on sterilization by the reaction characteristics of PEO, post-production sterilization of the final package by high-energy sources is not practical. Viable alternatives to conventional post production high energy sterilization methods include sterilization of the finished formulation in bulk form using autoclave protocols, followed by aseptic filling and packaging, or heat sterilization of the entire package in its final form.

One such method integrates production and sterilization of the polymer solution by use of a reactor vessel suitable for compounding the formula, vacuum degassing and heating the solution, under pressure, to a core temperature of 121° C. In practice, the polymer is compounded in pyrogen free water alone or alternatively with at least one polyalkylene glycol, degassed under vacuum and heated to 60° C. While under seal, the reactor vessel is back-filled with nitrogen gas, the solution heated to 121° C., held for 15 to 30 minutes at temperature and allowed to cool below 100° C. while stirring to achieve a homogenous solution prior to aseptic filling and packaging.

Alternatively, the polymer solution is compounded in a reactor vessel suitable for vacuum degassing and heating the solution. The polymer is compounded in pyrogen free water alone or preferably, slurried with polyalkylene glycol, followed by addition of water, degassed under vacuum while stirring and heated to 90° C. The polymer is then packaged into suitable containers and sterilized in final form according to conventional steam sterilization protocols.

The following examples illustrate preferred compositions and formulations that can be used to prepare solutions of PEO, suitable for use in medical ultrasound procedures. Those skilled in the art recognize that many variations are possible without violating the scope and spirit of the invention.

PEO used in the embodiments of this invention are selected from Union Carbide Sentry NF POLYOX WSR (water soluble-resins) grades. Formulations were prepared from grades that represent a range of molecular weights that produce solutions of PEO suitable for use as ultrasound couplants of this inventive device. These solutions each have acceptable viscosities (for example in the range of 1,000 to 250,000 centipoise) and mechanical properties, which produce an in vivo biocompatible ultrasound couplant that has acoustic properties similar to that of a target tissue (e.g. human tissue), and which render acceptable low levels of artifact, distortion and attenuation of the ultrasound energy.

Sentry (trade name of Union Carbide) NF grades (National Formulary Standard) of POLYOX selected for embodiments for this device are the WSR N-10 (100,000 mw.), WSR N-80 (200,000 mw.), WSR N-750 (300,000 mw.), WSR-205 (600,000 mw.), WSR 1105 (900,000 mw.), WSR N-60K (2,000,00 mw.), WSR 301 (4,000,000 mw.), and non-NF, WSR-308, (8,000,000 mw.), all of which are soluble in water at room temperature.

Using the manufacturing procedures previously outlined, solutions having various concentrations of WSR N-10, WSR N-80, WSR N-750, WSR 205, WSR 1105, WSR N-60K, WSR 301, and WSR-308 were prepared to determine their properties with changes in polymer concentration as well as to compare the relative differences between the solutions made from each of the grades.

Formulations within the ranges (wt. %) of the following examples were prepared:

EXAMPLE 1

Grade WSR N-10 PEO, Molecular Weight 100,000
Polymer Concentration Range: 1 to 45 wt. %
Propylene Glycol: 1 to 90%
Formula using WSR N-10
  35% WSRN-10
  65% pyrogen free water

EXAMPLE 2

Grade WSR N-10 PEO, Molecular Weight 100,000
Polymer Concentration Range: 1 to 45 wt. %
Propylene Glycol: 1 to 90%
Formula using WSR N-10
  20% WSR N-10
  40% USP propylene glycol
  40% pyrogen free water

EXAMPLE 3

Grade WSR N-80 PEO, Molecular Weight 200,000
Polymer Concentration Range: 1 to 40 wt. %
Propylene Glycol: 1 to 90%
Formula using WSR N-80
  15% WSR N-80
  85% pyrogen free water

EXAMPLE 4

Grade WSR N-80 PEO, Molecular Weight 200,000
Polymer Concentration Range: 1 to 40 wt. %
Propylene Glycol: 1 to 90%
Formula using WSR N-80
  12% WSR N-80
  45% USP propylene glycol
  43% pyrogen free water

EXAMPLE 5

Grade WSR N-750, PEO, Molecular Weight 300,000
Polymer Concentration Range: 1 to 30 wt. %
Propylene Glycol: 1 to 90%
Formula using WSR N-750
  6.0% WSR N-750
  94% pyrogen free water

EXAMPLE 6

Grade WSR N-750 PEO, Molecular Weight 300,000
Polymer Concentration Range: 1 to 30 wt. %
Propylene Glycol: 1 to 90%
Formula using WSR N-750
  5.0% WSR N-750
  60% USP propylene glycol
  35% pyrogen free water

EXAMPLE 7

Grade WSR 205, PEO, Molecular Weight 600,000
Polymer Concentration Range: 0.5 to 25%
Propylene Glycol: 1 to 90%
Formula using WSR 205
  4.75% WSR 205
  95.25% pyrogen free water

EXAMPLE 8

Grade WSR 205, PEO, Molecular Weight 600,000
Polymer Concentration Range: 0.5 to 25%
Propylene Glycol: 1 to 90%
Formula using WSR 205
  4.50% WSR 205
  18% USP propylene glycol
  77.50% pyrogen free water

EXAMPLE 9

Grade WSR 205 PEO, Molecular Weight 600,000
Polymer Concentration Range: 0.5 to 25 wt. %
Propylene Glycol: 1 to 90%
Formula using WSR 205
  4.25% WSR 205
  61% USP propylene glycol
  34.75% pyrogen free water

EXAMPLE 10

Grade WSR 1105, PEO, Molecular Weight 900,000
Polymer Concentration Range: 0.5 to 15 wt. %
Propylene Glycol: 1 to 90%
Formula using WSR 1105
  4.50% WSR 1105
  95.50.0% pyrogen free water

EXAMPLE 11

Grade WSR 1105, PEO, Molecular Weight 900,000
Polymer Concentration Range: 0.5 to 15 wt. %

Propylene Glycol: 1 to 90 wt. %
Formula using WSR 1105
  4.5% WSR 1105
  5.0% USP propylene glycol
  90.5% pyrogen free water

EXAMPLE 12

Grade WSR 1105, PEO, Molecular Weight 900,000
Polymer Concentration Range: 0.5 to 15 wt. %
Propylene Glycol: 1 to 90%
Formula using WSR 1105
  4.25% WSR 1105
  18% USP propylene glycol
  77.75% pyrogen free water

EXAMPLE 13

Grade WSR 1105, PEO, Molecular Weight 900,000
Polymer Concentration Range: 0.5 to 15 wt. %
Propylene Glycol: 1 to 90 wt. %
Formula using WSR 1105
  3.75% WSR 1105
  37.5% USP propylene glycol
  58.75% pyrogen free water

EXAMPLE 14

Grade WSR 1105, PEO, Molecular Weight 900,000
Polymer Concentration Range: 0.05 to 15 wt. %
Propylene Glycol: 1 to 90%
Formula using WSR 1105
  3.25% WSR 1105
  61.75% USP propylene glycol
  35% pyrogen free water

EXAMPLE 15

Grade WSR 1105, PEO, Molecular Weight 900,000
Polymer Concentration Range: 0.5 to 15 wt. %
Propylene Glycol: 1 to 90 wt. %
Formula using WSR 1105
  2.5% WSR 1105
  77.5% USP propylene glycol
  20% pyrogen free water

EXAMPLE 16

Grade WSR 1105, PEO, Molecular Weight 900,000
Polymer Concentration Range: 0.5 to 15 wt. %
Propylene Glycol: 1 to 90 wt. %
Formula using WSR 1105
  2.25% WSR 1105
  89.75% USP propylene glycol
  8.00% pyrogen free water

EXAMPLE 17

Grade WSR 1105, PEO, Molecular Weight 900,000
Polymer Concentration Range: 0.5 to 15 wt. %
Propylene Glycol: 1 to 90 wt. %
Formula using WSR 1105
  2.0% WSR 1105
  59.75% USP propylene glycol
  30% USP glycerol
  8.25% pyrogen free water

EXAMPLE 18

Grade WSR 1105, PEO, Molecular Weight 900,000
Polymer Concentration Range: 0.5 to 15 wt. %
Propylene Glycol: 1 to 90 wt. %
Formula using WSR 1105
  2.5% WSR 1105
  39.5% USP propylene glycol
  38% polyhydric alcohol (Sorbitol) (70% in water)
  20% pyrogen free water

EXAMPLE 19

Grade WSR N-60K, PEO, Molecular Weight 2,000,000
Polymer Concentration Range: 0.1 to 6 wt. %
Formula using WSR N-60K
  2% WSR N-60K
  98% pyrogen free water

EXAMPLE 20

Grade WSR N-60K, PEO, Molecular Weight 2,000,000
Polymer Concentration Range: 0.1 to 6 wt. %
Propylene Glycol: 1 to 45%
  Formula using WSR N-60K
  1.5% WSR N-60K
  18% USP propylene glycol
  80.5% pyrogen free water

EXAMPLE 21

Grade WSR N-60K PEO, Molecular Weight 2,000,000
Polymer Concentration Range: 0.1 to 6 wt. %
Propylene Glycol: 1 to 90%
Formula using WSR N-60K
  1.25% WSR N-60K
  63.75% USP propylene glycol
  35% pyrogen free water

EXAMPLE 22

Grade WSR 301, PEO, Molecular Weight 4,000,000
Polymer Concentration Range: 0.1 to 6 wt. %
Propylene Glycol: 1 to 90%
Formula using WSR 301
  2% WSR 301
  98% pyrogen free water

EXAMPLE 23

Grade WSR 308, PEO, Molecular Weight 8,000,000
Polymer Concentration Range: 0.05 to 6 wt. %
Propylene Glycol: 1 to 90%
Formula using WSR 308
  1% WSR 308
  99% pyrogen free water Subsequent to evaluation of data gathered from evaluation of polymers prepared from the above-mentioned Sentry NF Grades, WSR-1105 (900,000 mw.) and WSR-205 (600,000 mw.) were selected as the as the preferred polymers.

A preferred embodiment of an in vivo biocompatible, biodegradable ultrasound couplant is the shown by Example 9 that utilizes Sentry NF WSR205. The molecular weight (nominally 600,000) of this grade of polymer creates acceptable viscosities and rheologies at polymer concentrations of 5% and less, preferably 4%. Sentry NF WSR-1105 was, however, selected as a preferred polymer grade due to factors related to appearance, adhesion characteristics, rheology, ease of manufacture and economic factors. The most preferred embodiment is shown by Example 14 which is constituted as a 3.25% solution of WSR-1105 with 35% water and 61.75 wt. % propylene glycol, which produces viscosities of +/−13,000 centipoise (cps) as measured with a Brookfield viscometer using a #2 LVT spindle at 1.5 rpm.

Selection of this polymer for the most preferred embodiment producing such viscosity at a 3.25% polymer concentration, as compared to WSR-205, which requires 4.0% polymer, results in polymer cost savings and acceptable physical characteristics.

Sentry grade WSR-301, molecular weight 4,000,000, and the highest available molecular weight (8,000,000) resin WSR-308, produces equivalent viscosities with less polymer and greater clarity than a 3.25% solution of WSR-1105; however; it is less suitable for ultrasound use due to undesirable adhesive and tactile characteristics. Unlike transcutaneous gels of the prior art, a 3.25% solution of WSR-1105 is pseudoplastic and has sufficient film strength to adhere to the active face of the transducer and internal surface of probe covers to maintain desired acoustic coupling during rigorous ultrasound exams.

The embodiment of Example 14 demonstrates the ability to produce an increase in viscosity with less polymer as the propylene glycol to water ratio increases and is superior in this manner to the formulations where propylene glycol is secondary or absent. It is preferable that the weight percent of the polyalkylene glycol and/or polyhydric alcohol is greater than the weight percent of polyethylene oxide. Preferably, polyethylene oxide is present in an amount of about 1 wt. % to about 10 wt. %.

The propylene glycol to water weight ratio of (1.77/1) of the more preferred embodiment of Example 14 produces a higher viscosity with less polyethylene oxide (WSR 1105), thus reduces the cost of polymer and provides beneficial characteristics to the gel in the form of longer drying time, reduced stickiness, enhanced tactile qualities and a lower freezing point that improves freeze/thaw stability. It is preferred that the weight ratio of polyalkylene glycol and/or polyhydric alcohol to water be about 1.7:1 or more.

To illustrate the reduction in the amount of polymer as the amount of polyalkylene glycol is increased, polymer samples were prepared using 10%, 30% and 62% (wt. %) propylene glycol (PG), adding PEO WSR 1105 in the amounts of 4.5%, 4.0% and 3.0% (wt. %), respectively, and then adding to water in the amount required to equal 100%. These formulations all produced polymers with viscosities of 13,500 cps plus/minus 2.5%, as measured by a Brookfield Viscometer using a #2 Lvt @1.5 rpm.

FIG. 1 graphically illustrates the reduction in the amount of PEO WSR 1105 required as the weight percent (wt. %) of propylene glycol is increased from 10% to 62% thus indicating that equivalent viscosities can be produced with lesser amounts of PEO as the weight percentage of PG is increased.

Figure 2:
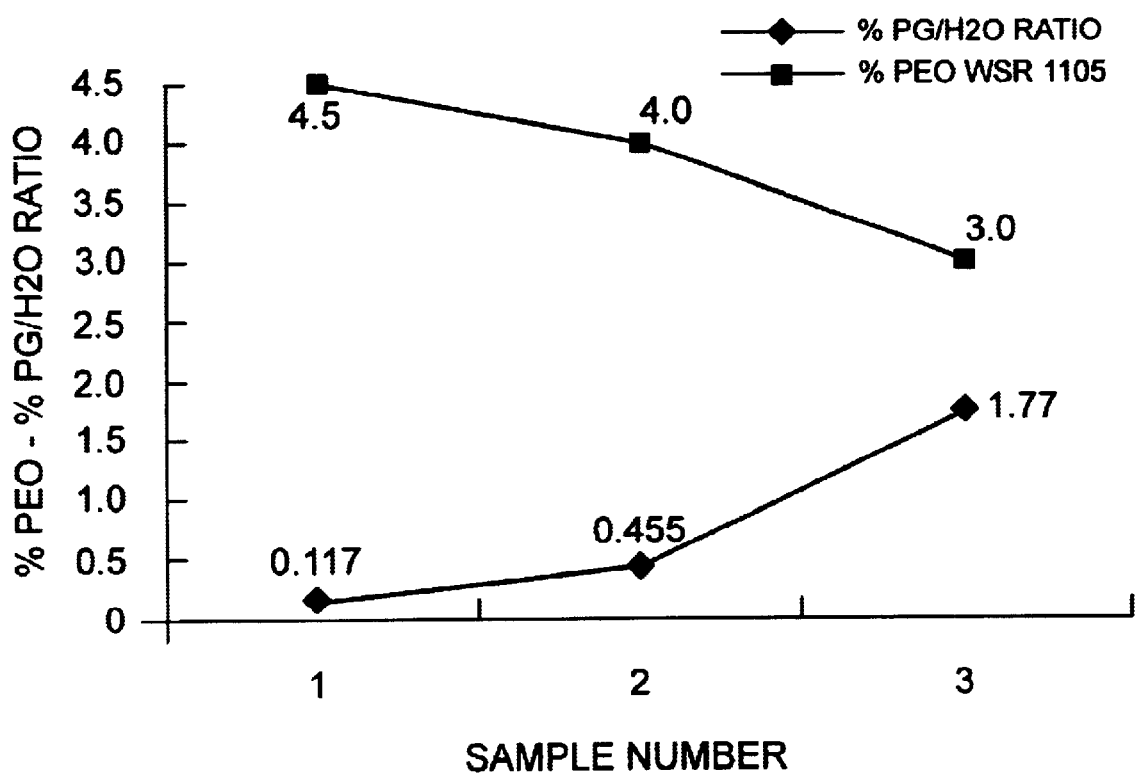
FIG. 2 illustrates the relationship between the ratio of PG/H2O and the amount of PEO required to produce equivalent polymer viscosities.

FIG. 2 graphically illustrates the increased thickening effect as it relates to all components in the system. Since water is the active component in the formulation for solution of the polyethylene oxide, PEO being insoluble in propylene glycol, the ratio of propylene glycol to water and the effective % of the polymer in the available water are controlling factors in production of equivalent viscosities while decreasing the polymer concentration. As the PG/$H_2O$ ratio increases, the amount of water available for solution of the polymer decreases. As the wt. % of propylene glycol increases from 10% to 62%, the concentration of the polymer in water increases from 5.26% to 8.57%, thus producing a higher viscosity as a PEO and water system, which results in higher viscosities than formulations containing more water, less propylene glycol and greater amounts of polymer. With the total volume of liquid held nearly constant, the amount of PEO required to produce a polymer solution of 13,500 cps (plus or minus) is less as the ratio of PGlH$_2$O increases, thus indicating enhancement in thickening ability when PEO is formulated in high ratio PG/$H_2O$ systems. Such enhancement provides the benefit of polymer cost reduction. Additionally, when fully formulated, the product of this inventive device provides longer drying times, due to the amount of humectants present, and a cosmetically pleasing feel as compared to less preferred formulations which contain lesser amounts of polyalkylene glycols and increased amounts of water.

In procedures where an ultrasound probe is covered by a protective sheath, as previously mentioned, the ultrasound couplants of the present invention not only provide acceptable lubricating and/or acoustic coupling properties on the outside of the protective sheath but also within the sheath (i.e. between the ultrasound probe and the sheath). Thus, in the event of rupture of the sheath, spillage of the inventive ultrasound couplant into a body cavity will not adversely affect the patient due to the in vivo biocompatibility of the couplants of the present invention.

In the same manner, puncture procedures under ultrasound imaging guidance, such as needle biopsies, can benefit from the present invention in that should the ultrasound couplant of this invention be carried by the needle into the body, it will be in vivo biocompatible, thus posing no harm to body cavity tissue.

It is also within the scope of the present invention to apply the inventive couplant directly to an organ or tissue, such as the eye, and then proceed with ultrasound imaging by contacting the couplant-coated organ or tissue with the active area of a transducer.

It is to be understood that while the present invention has been discussed with reference to medical ultrasound applications within a human body, it is not to be limited thereto. The present invention is also contemplated to be applicable within other animals such as in veterinary ultrasound.

While the invention has been described with reference to preferred embodiments it is to be understood that the invention is not limited to the particulars thereof. The present invention is intended to include process, formulation and modifications which would be apparent to those skilled in the art to which the subject matter pertains without deviating from the spirit and scope of the appended claims.

What is claimed is:

1. An ultrasound couplant and medical device lubricant comprising polyethylene oxide in an amount of about 0.05 wt. % to about 65 wt. %, at least one of polyalkylene glycols and polyhydric alcohols in the amount of about 1 wt. % to about 90 wt. %, and the balance water.

2. The ultrasound couplant and medical device lubricant of claim 1 wherein said polyalkylene glycols include fats and esters thereof.

3. The ultrasound couplant and medical device lubricant of claim 1 wherein said polyalkylene glycols comprise 2 or more carbon atoms.

4. The ultrasound couplant and medical device lubricant of claim 3 wherein said polyalkylene glycols comprise 2 to 6 carbon atoms.

5. The ultrasound couplant and medical device lubricant of claim 1 wherein said polyalkylene glycols comprise propylene glycol and/or glycerol.

6. The ultrasound couplant and medical device lubricant of claim 5 comprising propylene glycol.

7. The ultrasound couplant and medical device lubricant of claim 1 wherein said at least one of polyalkylene glycols and polyhydric alcohols is present in the amount of about 10 wt. % to about 70 wt. %.

8. The ultrasound couplant and medical device lubricant of claim 1 wherein said polyhydric alcohols comprise sorbitol.

9. An in vivo biocompatible ultrasound couplant and medical device lubricant comprising polyethylene oxide in an amount of about 0.05 wt. % to about 65 wt. %, at least one of polyalkylene glycols comprising two or greater carbon atoms and polyhydric alcohols in the amount of about 1 wt. % to about 90 wt. %, and the balance water.

10. The in vivo biocompatible ultrasound couplant and medical device lubricant of claim 9 wherein said polyalkylene glycols comprise propylene glycol.

11. The in vivo biocompatible ultrasound couplant and medical device lubricant of claim 10 comprising propylene glycol in an amount of about 10 wt. % to about 70 wt. %.

12. The in vivo biocompatible ultrasound couplant and medical device lubricant of claim 9 wherein said polyethylene oxide has a molecular weight of about 100,000 to about 2,000,000.

13. The in vivo biocompatible ultrasound couplant and medical device lubricant of claim 12 wherein said polyethylene oxide has a molecular weight of about 100,000 to about 1,000,000.

14. The in vivo biocompatible ultrasound couplant and medical device lubricant of claim 13 comprising about 0.5 wt. % to about 25 wt. % polyethylene oxide having a molecular weight of about 600,000, propylene glycol in an amount of about 1 wt. % to about 90 wt. %, and the balance water.

15. The in vivo biocompatible ultrasound couplant and medical device lubricant of claim 14 comprising about 4.0 wt. % polyethylene oxide, about 61.0 wt. % propylene glycol, and the balance water.

16. The in vivo biocompatible ultrasound couplant and medical device lubricant of claim 13 comprising about 0.05 wt. % to about 15 wt. % polyethylene oxide having a molecular weight of about 900,000, propylene glycol in an amount of about 1 wt. % to about 90 wt. %, and the balance water.

17. The in vivo biocompatible ultrasound couplant and medical device lubricant of claim 16 comprising about 3.25 wt. % polyethylene oxide, about 61.75 wt. % propylene glycol, and the balance water.

18. The in vivo biocompatible ultrasound couplant and medical device lubricant of claim 9 comprising polyethylene oxide in an amount of about 1 wt. % to about 10 wt. %.

19. The in vivo biocompatible ultrasound couplant and medical device lubricant of claim 9 wherein the wt. % of said at least one of polyalkylene glycols and polyhydric alcohols is greater than the wt. % of said polyethylene oxide.

20. The in vivo biocompatible ultrasound couplant and medical device lubricant of claim 9 having a weight ratio of said at least one of polyalkylene glycols and polyhydric alcohols to said water of about 1.7:1 or more.

* * * * *